United States Patent [19]

Nagahara et al.

[11] Patent Number: 5,998,182
[45] Date of Patent: Dec. 7, 1999

[54] DETERIORATION INHIBITOR FOR EMULSION-TYPE PROCESSING OIL AND METHOD FOR INHIBITING DETERIORATION OF EMULSION-TYPE PROCESSING OIL USING THE SAME

[75] Inventors: Hironari Nagahara, Higashi-Hiroshima; Hisao Yamasaki, Hiroshima; Takashi Miyama, Kashiwa; Nobuhiro Ito, Yamanashi-ken, all of Japan

[73] Assignee: Mazda Motor Corporation, Hiroshima, Japan

[21] Appl. No.: 08/853,397

[22] Filed: May 9, 1997

Related U.S. Application Data

[62] Division of application No. 08/410,789, Mar. 27, 1995, Pat. No. 5,652,135.

[30] Foreign Application Priority Data

Mar. 31, 1994 [JP] Japan .................................. 6-063278

[51] Int. Cl.$^6$ ...................................................... C12N 1/20
[52] U.S. Cl. ...................... 435/170; 435/252.1; 435/244; 424/93.4; 424/114; 424/115
[58] Field of Search ........................... 435/252.1, 244.17, 435/170; 424/93.4, 114, 115

[56] References Cited

PUBLICATIONS

Udalova, T.P., *Biol. Nauki*, 14(12), 80–85, 1971.
Kremenchutskii et al, *Mikrobiol. Zh.*, 51(5), 17–20, 1989.
Zadiraka et al., *Mikrobiol Zh.*, 53(4), 44–7, 1991.
Noeth et al., *Microb. Ecol.*, 16(2), 233–240, 1988.
Katz et al, *Bacteriol. Rev.*, vol. 41, pp. 447–474, 1977.
Rehm et al, "Biotechnology", 1981, p. 407, Verlagchemie.
Zaria et al, Central European J. of Public Health, No. 2, pp. 96–100, 1993.

*Primary Examiner*—Irene Marx
*Attorney, Agent, or Firm*—Martin Fleit

[57] ABSTRACT

Disclosed are a deterioration inhibitor for an emulsion-type processing oil comprising, as an active ingredient, a culture of a bacterial species selected from the group consisting of *Aerococcus viridans* BC-A-4 (Acceptance No. FERM BP-5042), *Bacillus brevis* BC-A-69 (Acceptance No. FERM BP-5041) and *Bacillus brevis* BC-A-3124 (Acceptance No. FERM BP-5043) and a method for inhibiting deterioration of an emulsion-type processing oil comprising adding such deterioration inhibitor to the emulsion-type processing oil and then allowing the bacteria contained in the deterioration inhibitor to proliferate. Since the propagation of the putrefying bacteria in the emulsion-type processing oils can be suppressed by the proliferation of the bacteria contained in the deterioration inhibitor, the working life of the emulsion-type processing oil can be prolonged.

15 Claims, 3 Drawing Sheets

DETERIORATION INHIBITOR FOR EMULSION-TYPE PROCESSING OIL AND METHOD FOR INHIBITING DETERIORATION OF EMULSION-TYPE PROCESSING OIL USING THE SAME

This is a divisional of application Ser. No. 08/410,789, filed Mar. 27, 1995 now U.S. Pat. No. 5,652,135.

FIELD OF THE INVENTION

The present invention relates to a deterioration inhibitor for an emulsion-type processing oil and a method for inhibiting deterioration of the emulsion-type processing oil by using it and, more particularly, to a deterioration inhibitor capable of prolonging the working life of an emulsion-type processing oil used for metal processing, such as a cutting and grinding oils, and a method for inhibiting deterioration of the emulsion-type processing oil using by it.

BACKGROUND OF THE INVENTION

Industrial processing oils such as cutting and grinding oils are essential to the metal processing field since they serve for the lubrication of sliding surfaces of tools, the cooling of tools and the materials to be cut and/or ground, the cleaning or removal of sludge, chips and the like, and thus are consumed in large quantities in that field. Among them, emulsion-type processing oils wherein the oils are emulsified with, for example, a surfactant have increasingly been used, because of the increased need of the improvement of the working environment, the reduction of fire risk required for the employment of unmanned system, and the like. Such emulsion-type processing oils have the following general composition.

TABLE 1

| Component | Amount (w/v %) |
| --- | --- |
| Mineral oil | 50–80 |
| Fat, fatty acid | 0–50 |
| High-pressure additive | 0–50 |
| Surfactant | 15–35 |
| Alkanolamine, alkali | 0–5 |
| Polyol, glycol | 0–10 |
| Organic inhibitor | 0–5 |
| Rut-proof microbicide | <2 |
| Anti-corrosive agent for copper alloy | <0.5 |
| Anti-foaming agent | <0.5 |
| Water | 0–10 |

Note:
this processing oil is diluted ten- to fifty-fold with water before use.

Such emulsion-type processing oils are useful in terms of their ability to reduce the fire risk, as described above. However, since the processing oils are used after they are diluted with water, it is inevitable to cause the propagation of aerobic or anaerobic bacteria, fungi and yeasts in the processing oils. More specifically, these microorganisms will propagate in the storage tanks and pipes through which the processing oils are circulated (reportedly, the concentration usually reaches from several ten millions to several hundred millions per ml) and, as a result, an offensive odor develops from their metabolites such as ammonia, methylamine, hydrogen sulfide, lower hydrocarbons, and volatile fatty acids. Thus, the pollution of the working environment by this odor has become a new problem. Further problem arises from the formation of the organic acids, such as lactic acid, which then lowers the pH of the emulsion and thus may result in the separation of the emulsion into oil and water (i.e., the loss of emulsion stability) and the metal corrosion.

In order to solve these problems, there have been taken the following measures: monitoring the emulsion-type processing oil by periodically measuring, for example, the concentration of the metabolites, pH, and the bacterium number; cleaning the tank and pipe; renewal of the processing oil; addition of an antiseptic agent; removal of fat components with an oil skimmer; making an aerobic condition by air-bubbling; and the like. However, these measures do not drastically solve the above problems. For example, an emulsion-type processing oil is pre-adjusted to a pH of about 9–10 to provide itself with anti-corrosive and anti-bacterial activities and, at such pH, the antiseptic agent which is added is degraded or deteriorated in the processing oil, and thus the desired antiseptic effect cannot be obtained by such agent. Further, in practice, an aerobic environment wherein the liquid continually flows and an anaerobic environment wherein the residue such as sludge and chips is deposited, co-exist in one system, and therefore various normal bacteria adapted to the respective environments, such as lactic acid-producing and sulfate-reducing bacteria, can be present and propagate in the same system. This makes it more difficult to select an effective measure for solving the above problems.

Under these circumstances, the emulsion-type processing oil is required to be completely replaced with fresh oil every three to six months. Since the replacement procedure including the subsequent thermal disposal of the waste oil consumes much material and time, the cost of the replacement procedure accounts for a considerable proportion of the production cost. Therefore, it is highly desirable to prolong the working life of the emulsion-type processing oil by a means which can readily be carried out at a low cost.

SUMMARY OF THE INVENTION

The object of the present invention is to provide a deterioration inhibitor for emulsion-type processing oils which can prolong the working life of the emulsion-type processing oils by a simple means without either raising the production cost or impairing their performance, and a method for inhibiting deterioration of the emulsion type processing oils.

Figure 1:
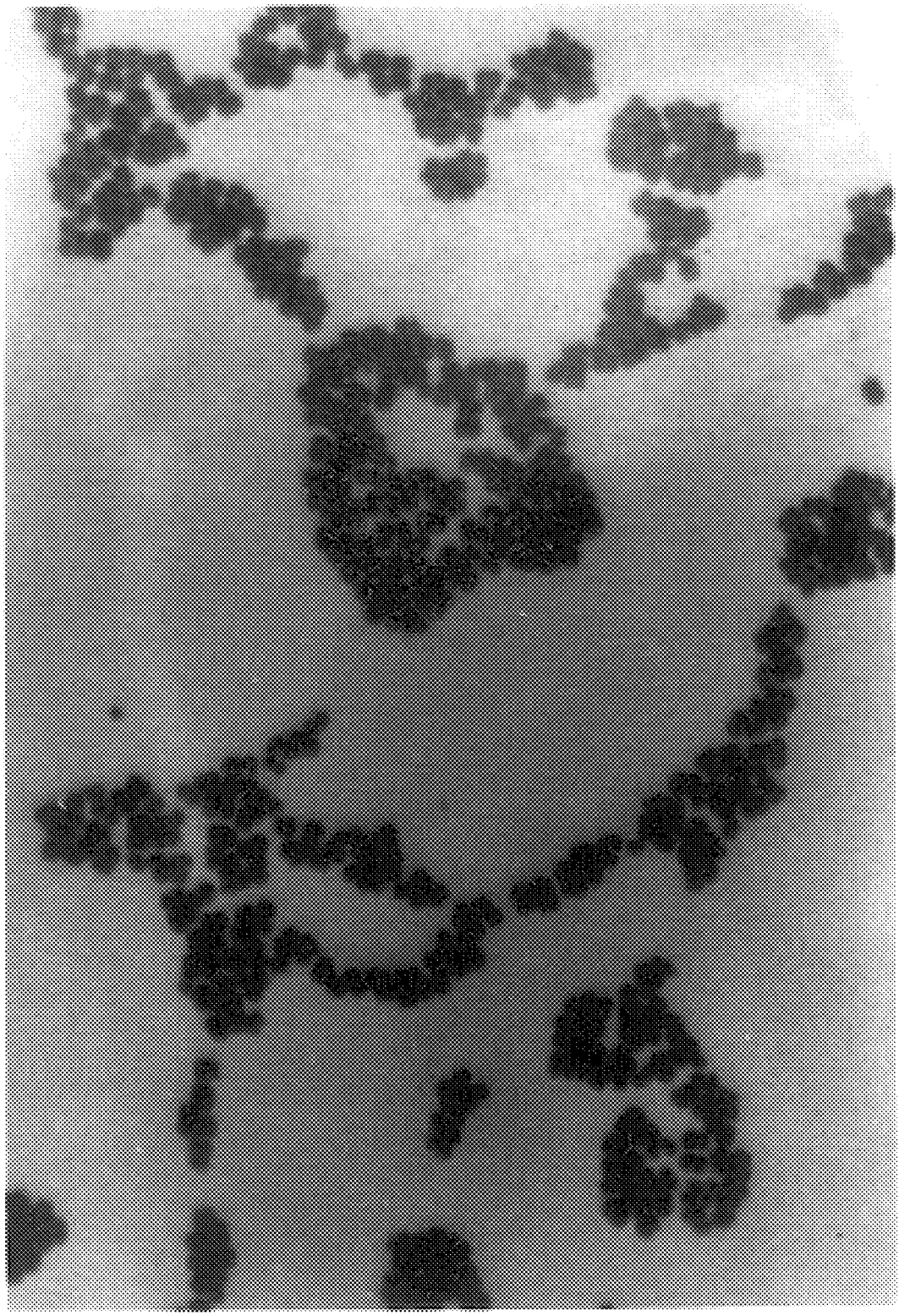
FIG. 1 is the microphotograph showing the morphology of *Aerococcus viridans* BC-A-4.

Hitherto, in the art where a microorganism is used in an open system such as brewing industry, the property that a certain microorganism can suppress growth or proliferation of other microorganisms present in the same system via its own proliferation, i.e., "ecological defense property of microorganism" has substantially been utilized. Since it appears impossible to inhibit the propagation of normal bacteria in the emulsion-type processing oils by a conventional method, the present inventors have made an effort to apply the foregoing defense property to this approach so as to achieve the above object by intentionally propagating the bacteria which neither develop an offensive odor via their metabolism, nor impair the emulsion stability, in the emulsion-type processing oils. Consequently, it has been found that there exist alkaliphilic bacteria which can grow or proliferate under hard aerobic and anaerobic conditions of the emulsion-type processing oils even at a pH of about 9–10 and do not have any adverse influence upon the emulsion-type processing oils. The present invention has been made on the basis of this finding.

More specifically, the present invention relates to a deterioration inhibitor for emulsion-type processing oils comprising, as an active ingredient, a culture of a bacterial species selected from the group consisting of *Aerococcus viridans* BC-A-4 (Acceptance No. FERM P-14172), *Bacillus brevis* BC-A-69 (Acceptance No. FERM P-14171) and *Bacillus brevis* BC-A-3124 (Acceptance No. FERM P-14173).

The present invention also relates to a method for inhibiting deterioration of emulsion-type processing oils comprising adding such a deterioration inhibitor to the emulsion-type processing oil and then allowing the bacteria contained in the deterioration inhibitor to proliferate.

DETAILED DESCRIPTION OF THE INVENTION

The emulsion-type processing oils which may be treated by the deterioration inhibitor according to the present invention are those processing oils which are diluted with water before use as described above and which contain an emulsifier such as a surfactant. The term "processing oils" as used herein denotes all oil components which may industrially be used, such as cutting, grinding, press and hydraulic oils, and metal detergents. Specific examples of such emulsion-type processing oils include Multan (commercially available from Henckel Hakusui), Yushiroken (commercially available from Yushiro Chemical Industries), Shimilon (commercially available from Daido Chemical Industries), and Emulcut (commercially available from Kyodo Yushi).

The term "inhibiting deterioration" as used herein means to solve the various problems which arise from the propagation of aerobic or anaerobic bacteria, fungi, and yeasts in the emulsion-type processing oils, for example, the pollution of the working environment by the development of the offensive odor, the separation of the emulsion into oil and water as well as metal corrosion (rusting, etc.) caused by the pH lowered by the formation of the organic acids such as lactic acid. That is, the term means to solve all problems which cause the impairment of the performance of the emulsion-type processing oils. The subjects to which the deterioration inhibitor according to the present invention may be applied include the emulsion-type processing oils not only during but also before use, for example, those being in preservation.

The cultures contained in the deterioration inhibitor according to the present invention as an active ingredient are those of the following bacteria: *Aerococcus viridans* BC-A-4, *Bacillus brevis* BC-A-69, or *Bacillus brevis* BC-A-3124. These bacteria were deposited on Feb. 22, 1994 under Acceptance Nos. FERM P-14172, FERM P-14171, and FERM P-14173, respectively, with National Institute of Bioscience and Human Technology (NIBHT) (old name Fermentation Reseach Institute (FRI)), 1-1-3, Higashi, Yatabe-cho, Tsukuba-gun, Ibaraki-ken, JAPAN. In this connection, these bacteria were transferred in NIBHT on Mar. 20, 1995 from the national deposition to the international deposition under Budapest Treaty under Acceptance Nos. FERM BP-5042, BP-5041 and BP-5043, respectively.

Among these bacteria, *Aerococcus viridans* BC-A-4 was identified and designated according to Bergey's Manual of Systematic Bacteriology from the mycological properties shown in Table 2 below nd the morphological characteristics (see the microphotograph of FIG. 1).

Figure 2:
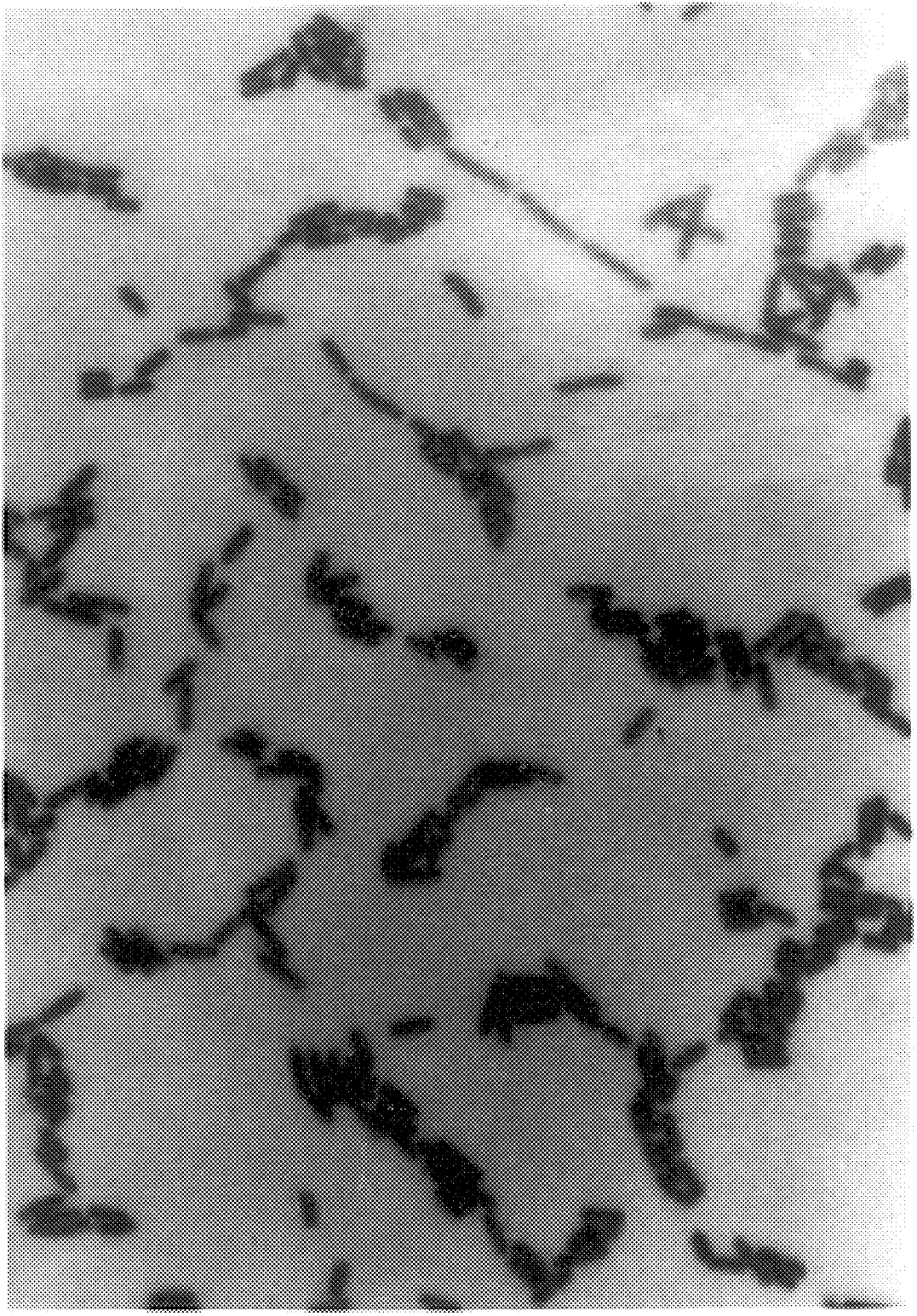
FIG. 2 is the microphotograph showing the morphology of *Bacillus brevis* BC-A-69.
Figure 3:
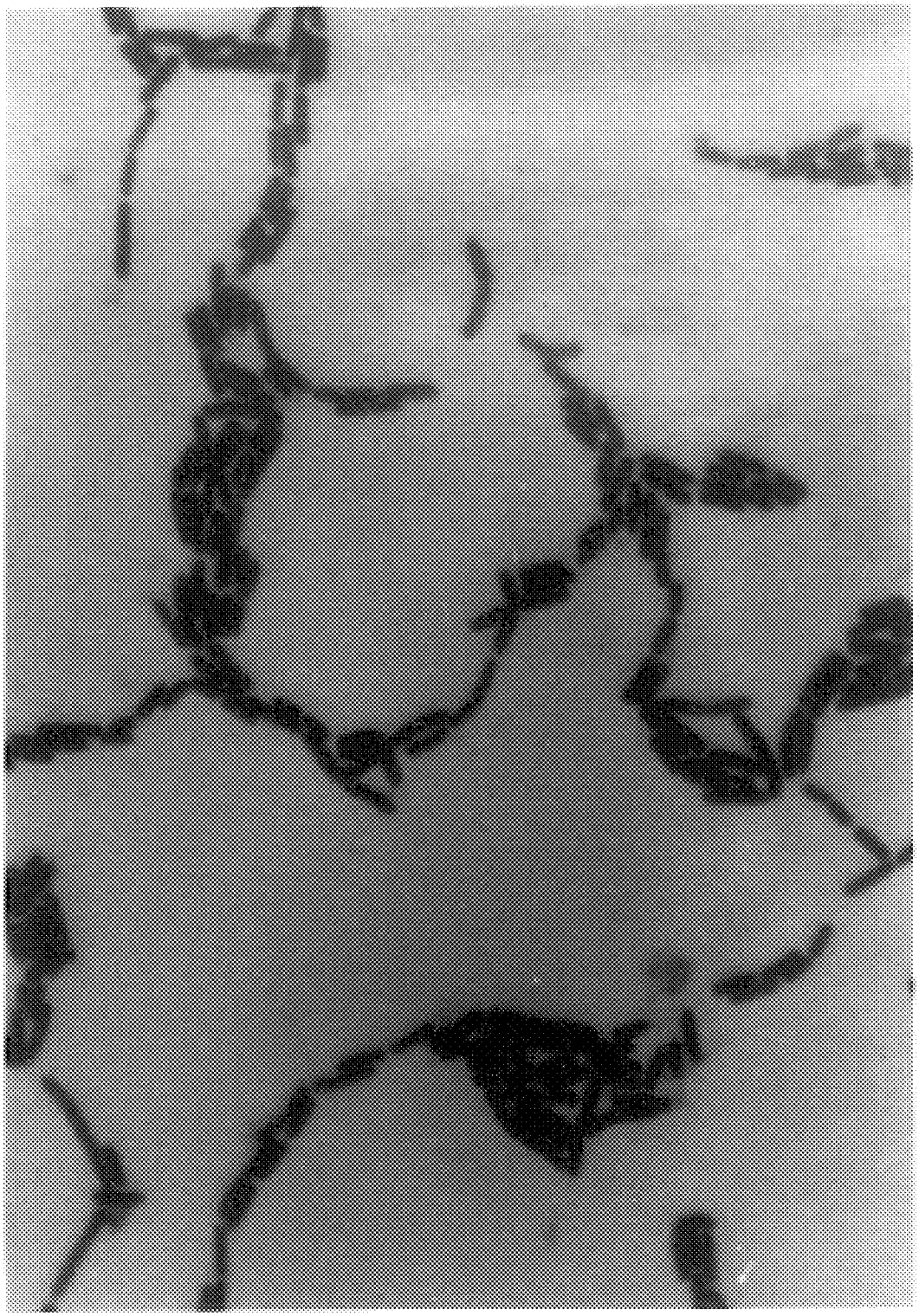
FIG. 3 is the microphotograph showing the morphology of *Bacillus brevis* BC-A-3124.

*Bacillus brevis* BC-A-69 and *Bacillus brevis* BC-A-3124 were also identified and designated according to Bergey's Manual of systematic Bacteriology from the mycological properties shown in Table 2 below and the morphological characteristics (see the microphotographs of FIGS. 2 and 3). These bacteria are considered to be very near relatives each other.

The mycological properties of these bacteria are shown in Table 2, below. All of the bacteria were isolated from soil taken from the site where the metal workshop was built, in Hofu-shi, Yamaguchi-ken, JAPAN.

TABLE 2

|  |  | A. viridans BC-A-4 | B. brevis BC-A-69 | B. brevis BC-A-3124 |
|---|---|---|---|---|
| (a) | Morphological properties | | | |
| | Cell form | spherical | rod | rod |
| | Colony color | white | pale yellow | pale yellow |
| | Cell size (μm) | | | |
| | Short diameter | 0.5–0.8 | 0.5–0.6 | 0.5–0.6 |
| | Long diameter | 0.5–0.8 | 1.2–2.0 | 1.2–2.0 |
| | Presence of flagella | not present | present (peripheral) | present (peripheral) |
| (b) | Culturological properties | | | |
| | Broth gelatin stab culture (liquidization of gelatin) | – | – | weak |
| (c) | Physiological properties | | | |
| | Gram staining | positive | positive | positive |
| | Reduction of nitrate salt | – | weak | weak |
| | VP test | negative | negative | negative |
| | Urease | negative | negative | negative |
| | Oxidase | negative | positive | positive |
| | Catalase | weak | positive | positive |
| | O–F test | fermentable | negative | negative |
| | Assimilation of saccharides | | | |
| | L-arabinose | – | – | – |
| | D-xylose | – | – | – |
| | D-glucose | – | – | – |
| | D-fructose | + | – | – |
| | Maltose | + | – | – |
| | Sucrose | + | – | – |
| | Lactose | + | – | – |
| | Trehalose | + | weak | weak |
| | Mannitol | + | weak | – |
| (d) | Other properties | | | |
| | Degradation of esculin | | positive | positive |
| | Degradation of arginine | negative | negative | negative |
| | Growth under 5% NaCl | | weak | weak |
| | Growth at 30° C. | + | + | + |
| | Growth at 50° C. | | – | – |
| (e) | Chemical/taxonomical property | | | |
| | Base composition of DNA (GC content) | | 44.3% | 44.3% |

The deterioration inhibitor according to the present invention may be any of those inhibitors so long as such inhibitors comprise a culture of one or more species of the bacteria described above, and may be in any form, such as solid, powder or liquid. The deterioration inhibitor according to the present invention will be described in detail hereinbelow by illustrating one embodiment of the preparation thereof.

First, soil containing the desired bacteria is extracted with a liquid consisting of saline and a mixed solution (having a pH of preferably about 8–11, more preferably about 9–10) of sodium carbonate and sodium bicarbonate. The extract is then cultured in an alkaline liquid medium (having a pH of preferably about 8–11, more preferably about 9–10). When the pH of the medium is lower than 8, the desired bacteria can not be separated and proliferated. On the other hand, when the pH of the medium is higher than 11, the desired bacteria can not be proliferated.

If necessary, the extract may be cultured in an alkaline liquid medium further containing a proliferation accelerator. The proliferation accelerator include ferrous and ferric salts such as a ferrite, having a spinel, structure preferred example is a magnetite.

The proliferation accelerator may be used in a saline solution having a concentration of, generally, 0.005~0.5% by weight, preferably 0.01~0.1% by weight. The preferred example of the proliferation accelerator includes a ferrite having a spinel structure. The ferrous and ferric salts may be generally contained in the saline solution in an amount of generally 0.0001~0.001% by weight, preferably 0.0002~0.0005% by weight. Preferred proliferation accelerator is PWS stock solution (commercially available from Kabushiki Kaisha Jinen). PWS stock solution has the following composition:

| Sodium chloride | 0.3% by weight |
| Magnetite | 0.001%, as Fe |
| Purified Water | to 100.00% |

Addition of PWS stock solution makes water clusters uniformly small and thereby can enhance the physiological action of the bacteria and can allow the cultivation to smoothly proceed.

Subsequently, the bacteria are subcultured in solid media and separated into each species. Next, one or more species of the bacteria thus isolated are inoculated into an emulsion-type processing oil which has been adjusted to the certain pH value (e.g., pH of 9–10) and, preferably, the same processing oil as that to be treated with the present deterioration inhibitor, and then cultured.

The cultivation is usually carried out at about 37° C. for about 3 days to 3 weeks, preferably for 5 days to 10 days. In this case, a proliferation accelerator may be used in the culture media.

The resultant culture has usually a pH of 8–11, preferably 9–10 for the reason stated above.

The optimum bacterial number (bacterial concentration) of the culture largely depends on the kind of the processing oils, the conditions for use such as temperatures, and the like. However, the bacterial concentration of the culture is generally $10^6$/ml~$10^9$/ml, preferably $10^7$/ml~$10^8$/ml.

This culture may be used as the deterioration inhibitor as it is. The culture may be lyophilized to reduce it into powder, or it may be supported on a solid or powdery carrier or carrier medium which is dispersible in the emulsion-type processing oil so as to form a suspension. If necessary, the culture may be recultured to optimize the bacterial number to the above bacterial concentration, prior to the addition to the processing oil to be treated.

Next, the present method for inhibiting deterioration of emulsion-type processing oils will be described hereinbelow. This method, for example, when it is applied to a practically operating machine, is carried out by adding the present deterioration inhibitor to a fresh emulsion-type processing oil and then replacing whole or a part of the used up emulsion-type processing oil with a fresh oil. In this case, if necessary, circulating storage tanks and pipes may be cleaned prior to the replacement. Since an emulsion-type processing oil is usually used at ordinary room temperature, it is not generally required to pay attention to temperatures of the oil. However, when the temperature is considerably high, it is preferred to use a cooling means.

The amount of the deterioration inhibitor depends on the bacterial number (concentration) contained therein, the conditions for use such as temperature, the quantity of the emulsion-type processing oil to be replaced (whether in whole or in part) and the like. However, the deterioration inhibitor is generally added to emulsion-type processing oils to be treated in an amount of 0.01~0.5% by weight, preferably 0.05~0.1% by weight of the processing oil.

The deterioration inhibitor may be added to the emulsion-type processing oils in any type of form such as powder, solution and the like, without any further treatment.

It is preferred to adjust the deterioration inhibitor to the same pH as the emulsion-type processing oil to be treated.

After the deterioration inhibitor is added to emulsion-type processing oil to be treated, the emulsion-type processing oil is circulated under the practical condition. During this circulation, the bacteria contained in the deterioration inhibitor proliferate and exhibit the ecological defense, and thus suppress the proliferation of other unfavorable microorgamisms such as bacteria, fungi and yeasts present in the same system.

Although the present invention will now be illustrated in detail by referring to the following Examples, it should be understood that the scope of the present invention should not be limited by these examples.

EXAMPLES

Example 1

(1) Harvesting and Cultivation of Bacterial Clusters

A commercially available emulsion-type processing oil was spread over bare ground of weak alkaline soil, and then covered with a vinyl sheet. After one week aging, a soil sample was taken. Next, 100 g of this sample was immersed for 24 hours in an isobaric saline which had been adjusted to pH of about 10 with a mixed solution of sodium carbonate and sodium bicarbonate to extract the bacteria contained in the sample. The extract was then incubated for 7 days at 37° C. in alkaline liquid medium having the composition shown in Table 3 below.

TABLE 3

| Component | Amount (w/v %) |
|---|---|
| Glucose | 1.0 |
| Polypeptone | 0.6 |
| Yeast extract | 0.6 |
| Liquid paraffin | 1.0 |
| Polysorbate 80 (commercially available from Kao) | 1.0 |
| Sorbitan monooleate | 0.5 |
| Sodium carbonate | 0.56 |
| Sodium bicarbonate | 0.54 |
| Potassium hydrogen phosphate | 0.10 |
| Magnesium sulfate | 0.02 |
| PWS stock solution (commercially available from Kabushiki Kaisha Jinen) | 0.1 |
| Purified water | to 100.00 |

(2) Isolation of Bacteria

The bacteria contained in the alkaline liquid culture were transplanted in solid plate media by adding agar to the alkaline liquid culture to a concentration of 1.5% by weight so as to solidify it, and isolation culturing was conducted under both aerobic and anaerobic conditions. Afterward, with respective isolation subculturing, *Aerococcus viridans* BC-A-4, *Bacillus brevis* BC-A-69 and *Bacillus brevis* BC-A-3124 were isolated.

(3) Preparation of Deterioration Inhibitor

A culture medium was prepared by diluting Multan 780 (commercially available from Henckel Hakusui) with water to a concentration actually used, adjusting the dilution to pH 9.5 with a sodium carbonate buffer, and then adding PWS stock solution to a concentration of 0.1 w/v%. This culture medium was then inoculated with each of the three bacterial species above-isolated, incubated for one week at 37° C., and then adjusted to a bacterial concentration of $10^6$–$10^7$/ml to give the deterioration inhibitor.

Test Example 1

Each of the three bacterial species isolated in Example 1 (2) was used to carry out the proliferation test in the cutting oil having the composition shown in Table 4 below and the bacterium number was counted as number of colonies in the oil after proliferation. Proliferation test was also conducted in the same manner except that PWS stock solution was omitted. The results are shown in Table 5 below.

TABLE 4

| Component | Amount (w/v %) |
| --- | --- |
| Liquid paraffin | 25.0 |
| Chlorinated paraffin | 15.0 |
| Silicone oil | 1.0 |
| Self-emulsifying glycerin fatty acid ester | 10.0 |
| Ethylene oxide addition product of higher alcohol | 10.0 |
| Sucrose fatty acid ester | 5.0 |
| Sodium alkyl sulfonate | 5.0 |
| Alkanolamine | 10.0 |
| Propylene glycol | 10.0 |
| PWS stock solution | 1.0 |
| Purified water | to 100.0 |

TABLE 5

| Cutting oil | Cultivation condition | Bacterium number (/ml) |
| --- | --- | --- |
| with PWS | 37° C., for 7 days | $5 \times 10^7$ |
| without PWS | 37° C., for 7 days | $1 \times 10^2$ |

PWS = PWS stock solution

As can be seen from Table 5, the bacteria is more proliferative in the presence of PWS stock solution than in the absence of PWS stock solution.

Example 2

The following three test liquids were prepared.

Test (Control) liquid No.1: dilution of the emulsion-type cutting oil on the market (Emulcut (Commercially available from Kyodo Yushi)), which was prepared by diluting twenty-fold with water as practically used; Test liquid No.2: Test liquid No.1 to which the deterioration inhibitor obtained in Example 1 was added to a concentration of 1 w/v%; and Test liquid No.3: Test liquid No.1 to which not only the deterioration inhibitor obtained in Example 1 but also PWS stock solution as a microorganism proliferation accelerator were added to concentrations of 1 and 0.1 w/v%, respectively.

These liquids were tested according to the following method and observed for the proliferation state.

Test Method

Each of the test liquids was maintained in an open vessel for 6 months at constant temperature of 37° C. while stirring. During this period, the evaporation loss of water was replenished with purified water. Initial pH was 9.5 in all cases. Initial bacterium numbers of Test liquid Nos.2 and 3 were $10^6$–$10^7$/ml. The results are shown in Table 6 below.

TABLE 6

| Test liquid | Final pH value | Bacterium number | Emulsion state | Odor |
| --- | --- | --- | --- | --- |
| No. 1 | 7.25 | $10^5$/ml | B → D | A → C |
| No. 2 | 8.05 | $10^6$/ml | B → C | A → B |
| No. 3 | 8.55 | $10^9$/ml | B → B | A → A |

Note:
the following observation evaluation scales were used:
for odor,

A: good
B:
C: slightly offensive
D:
E: very offensive; and
for emulsion state,

A; not separated
B;
C; slightly separated
D;
E; completely separated.

As can be seen from Table 6, Test liquid Nos.2 and 3 showed the increase in the bacterium number and, consequently, the decrease in the pH was prevented as low as possible, which, in turn, resulted in the excellent effect on the emulsion stability and the inhibition of the offensive odor.

Example 3

Test liquid Nos.4 to 9 shown in Table 7 were prepared and tested in the same manner as Example 2 except that a test period of one month was employed. The results are shown in Table 8 below.

TABLE 7

| | |
| --- | --- |
| No. 4 | The same emulsion-type cutting oil as used in Example 2 (Test liquid No. 1), except that it was used in an actual workshop until it was required to be replaced with the fresh oil (pH 7.50, bacterium number $10^7$/ml) |
| No. 5 | Test liquid No. 3 used in Example 2 (pH 9.50, bacterium number $10^8$/ml) |
| No. 6 | Test liquid No. 5 to which Test liquid No. 4 adjusted to a bacterium number of $10^4$/ml was added to a concentration of 5 w/v % |
| No. 7 | Test liquid No. 5 to which Test liquid No. 4 adjusted to a bacterium number of $10^5$/ml was added to a concentration of 5 w/v % |
| No. 8 | Test liquid No. 5 to which Test liquid No. 4 adjusted to a bacterium number of $10^6$/ml was added to a concentration of 5 w/v % |
| No. 9 | Test liquid No. 5 to which Test liquid No. 4 adjusted to a bacterium number of $10^7$/ml was added to a concentration of 5 w/v % |

TABLE 8

| Test liquid | Final pH value | Bacterium number | Emulsion state | Odor |
|---|---|---|---|---|
| No. 4 | 7.25 | $10^5$/ml | C → D | C → D |
| No. 5 | 8.75 | $10^9$/ml | A → A | A → A |
| No. 6 | 8.70 | $10^8$/ml | A → B | A → A |
| No. 7 | 8.25 | $10^8$/ml | B → B | A → B |
| No. 8 | 7.97 | $10^6$/ml | B → B | A → C |
| No. 9 | 8.02 | $10^6$/ml | B → C | A → C |

Note:
the evaluation scales for odor and emulsion state are identical with those of Table 6.

As can be seen from Table 8, even when the used up cutting oil in which putrefying bacteria were proliferated, remained in the concentration of 5 w/v%, the advantages of the present invention were obtained virtually without difficulty. Therefore, according to the present invention, even when a cutting oil which is putrefied and develops an offensive odor is withdrawn from a practically operating plant through which the oil is circulated and a fresh cutting oil containing the present inhibitor is immediately introduced into the plant without any cleaning procedure, it was confirmed that the plant could be practically operated.

Example 4

In the workshop (the first speed regulator workshop in the head factory of Matsuda Kabushiki Kaisha) being practically at work, the circulating plant having 12 cutting and grinding machines and containing 10 tons of cutting oil in total were divided into two groups each having 6 machines. One group contains machines 1–6 which are untreated by this invention and therefore is a control group. The other group contains machines 7–12 which are treated by this invention and therefore is a trial group. Using these two groups, continuous, practical runs were conducted in the daytime over 6 months. The cutting and grinding oil used was Emulcut (Commercially available from Kyodo Yushi). In the trial group, the deterioration inhibitor of Example 1 and PWS stock solution were added to the oil to concentrations of 1 w/v% and 0.1 w/v%, respectively. Prior to the practical runs, the oils were circulated through the machines for 6 hours and allowed to stand overnight. The results are shown in Table 9.

TABLE 9

|  | Control group machines 1–6 | Trial group machines 7–12 |
|---|---|---|
| Odor evaluation | A → E | A → AB |
| Emulsion stability | A → D | A → B |
| Minimum to maximum temperature | 18–33° C. | 18–33° C. |
| Minimum to maximum pH value | 7.65–9.18 | 8.35–9.02 |
| Number of times of pH adjustment | 3–4 | 1–2 |
| Viable bacterium number | $10^3$–$10^6$/ml | $10^4$–$10^8$/ml |

Note:
the evaluation scales for emulsion state and odor are identical with those of Table 6.

From the results in Table 9, it was confirmed that the method of the present invention could advantageously be used in the practical workshop in terms of the following points:

(1) While the average number of times of pH adjustment per month is 0.5 in the conventional method, it was reduced to 0.2 by the present invention. This indicates that once the pH is adjusted to an optimum value at the time of the replacement with a fresh oil, the value can be maintained without further pH adjustment until the next replacement;

(2) Even after removal of sludge and chips, and the removal of an oil layer with an oil skimmer, no separation of the emulsion was observed;

(3) The workers involved in the operation of the machines treated by the present invention did not complain of the pollution of the working environment by an offensive odor.

(4) The present invention did not adversely affect working efficiency of the practical processes such as tapping and centerless grinding. Also, no development of corrosion or rust was observed on the processed metal. From these, it was also confirmed that while the deterioration inhibitor according to the present invention, i.e., the bacteria contained therein inhibit propagation of the putrefying bacteria, they do not adversely affect the quality of the grinding oil and the like and the processed metal.

Thus, in the trial group, the great advantages were obtained and there was no need of replacement of the cutting oil and the like even after 6 months from the last replacement. In contrast, in the control group, the development of the offensive odor and the separation of the emulsion were observed and the replacement was needed within 6 months from the last replacement. By sampling and culturing the processing oil taken from the operation zone for the trial group during or after the runs for 6 months, white micrococci and pale yellow bacilli were observed. On the other hand, the normal bacteria and *Bacillus subtilis* which may cause putrefaction were observed in the samples taken from the operation zone for the control group.

The deterioration inhibitor of the present invention comprises a culture of *Aerococcus viridans* BC-A-4, *Bacillus brevis* BC-A-69 or *Bacillus brevis* BC-A-3124. They are alkaliphilic bacteria. The method for inhibiting the deterioration according to the present invention comprises use of such a deterioration inhibitor.

According to the present invention, the propagation of the unfavorable putrefying bacteria and the like in the emulsion-type processing oils can be suppressed via the ecological defense property exhibited by the proliferation of the alkaliphilic bacteria. In addition, the alkaliphilic bacteria do not impair performance of the emulsion-type processing oils.

Therefore, the present invention can solve the problems associated with the conventional emulsion-type processing oils, for example, development of the offensive odor by putrefaction of the oils which was usually observed within about 3 to 6 months after the replacement with the fresh oil, separation of the emulsion, and metal corrosion caused by the lowered pH, and can greatly prolong the working life of the emulsion-type processing oils. Further, the present invention can lower the cost of the waste oil disposal. Therefore, the production cost can also be lowered sharply.

What is claimed is:

1. A method for inhibiting deterioration of an emulsion-type processing oil comprising the steps of:
   adding a deterioration inhibitor comprising a culture of a bacterial strain selected from the group consisting of *Aerococcus viridans* BC-A-4 FERM BP-5042, *Bacillus brevis* BC-A-69 FERM BP-5041 and *Bacillus brevis* BC-A-3124 FERM BP-5043, and
   allowing said strain to proliferate in the emulsion-type processing oil.

2. The method of claim 1, further comprising the step of culturing said strain in an emulsion-type processing oil to obtain said culture.

3. The method of claim 1, wherein said culture contains said strain in an amount of $10^6$–$10^9$ bacteria/ml.

4. The method of claim 3, wherein said culture contains said strain in an amount of $10^7$–$10^8$ bacteria/ml.

5. The method of claim 1, wherein said culture has a pH of 8–11.

6. The method of claim 5, wherein said culture has a pH of 9.0–10.

7. The method of claim 1, further comprising the step of accelerating proliferation of said strain with a proliferation accelerator.

8. The method of claim 7, wherein said proliferation accelerator is a ferrous and ferric salt.

9. The method of claim 8, wherein said ferrous and ferric salt is a ferrite having a spinel structure.

10. The method of claim 1, further comprising the steps of cleaning inside of machine equipment so that microorganisms proliferating in the emulsion-type processing oil which are different from the bacterial strain do not remain in the machine equipment and using the emulsion-type processing oil in the machine equipment after adding said deterioration inhibitor.

11. The method of claim 10, further comprising the step of operating the machine equipment for a prescribed period of time after adding said deterioration inhibitor so that the bacterial strain in the emulsion-type processing oil proliferates.

12. A method for preventing deterioration of an emulsion-type processing oil during its utilization in machine equipment while said machine equipment is operated, comprising the steps of:

(1) preparing as a deterioration inhibitor a culture of a bacterial strain selected from the group consisting of *Aerococcus viridans* BC-A-4 FERM BP-5042, *Bacillus brevis* BC-A-69 FERM BP-5041, *Bacillus brevis* BC-A-3124 FERM BP-5043 and combinations thereof which produces no offensive odor due to metabolized product in an emulsion-type processing oil;

(2) adding the deterioration inhibitor into a fresh emulsion-type processing oil to form a bacterial strain containing emulsion-type processing oil for use in a machine equipment;

3) introducing said bacterial strain containing emulsion-type processing oil into a machine equipment which uses said processing oil during operation of said machine equipment, and 4) maintaining said bacterial strain containing emulsion-type processing oil above a pH of about 8 as it is utilized during operation of said machine equipment to prevent deterioration of the emulsion-type processing oil.

13. The method of claim 12, wherein step (4) is carried out by maintaining said bacterial strain containing emulsion-type processing oil at a pH of 9.0 to 9.

14. A method for preventing deterioration of an emulsion-type processing oil during its utilization in a machine equipment while said machine equipment is operated, comprising the steps of, (1) preparing as a deterioration inhibitor a culture of a bacterial strain selected from the group consisting of *Aerococcus viridans* BC-A-4 FERM BP-5042, *Bacillus brevis* BC-A-69 FERM BP-5041, *Bacillus brevis* BC-A-3124 FERM BP-5043 and combinations thereof which produces no offensive odor due to metabolized product in a fresh emulsion-type processing oil which is to be used in a machine equipment;

(2) adding the deterioration inhibitor to a fresh emulsion-type processing oil to form a bacterial strain containing emulsion-type processing oil (3) removing used-up emulsion-type processing oil from a machine equipment in which said used-up emulsion-type processing oil has been utilized during operation of said machine equipment;

(4) cleaning said machine equipment after removal of the used-up emulsion-type processing oil;

(5) introducing said bacterial strain containing emulsion-type processing oil into said cleaned machine equipment to be utilized during operation of said machine equipment; and (6) maintaining said bacterial strain containing emulsion-type processing oil at a pH above about 8, as it is being utilized during operation of said machine equipment to prevent deterioration of said emulsion-type processing oil.

15. A method for operating a machine equipment containing an emulsion-type processing oil that is utilized during operation of the machine equipment that comprises the steps of:

(1) using as the processing oil of the machine equipment, an emulsion-type processing oil into which has been added a culture of a bacterial strain selected from the group consisting of *Aerococcus viridans* BC-A-4 FERM BP-5042, *Bacillus brevis* BC-A-69 FERM BP-5041, *Bacillus brevis* BC-A-3124 FERM BP-5043 and combinations thereof as a deterioration inhibitor, and (2) maintaining said emulsion-type processing oil containing said bacterial strain above a pH of about 8 as it is being utilized during operation of said machine equipment to prevent deterioration of said emulsion-type processing oil.

* * * * *

UNITED STATES PATENT AND TRADEMARK OFFICE
CERTIFICATE OF CORRECTION

PATENT NO. : 5,998,182
DATED : December 7, 1999
INVENTOR(S) : Hironari Nagahara, Hisao Yamasaki, Takashi Miyama, Nobuhiro Ito It is certified that error appears in the above-identified patent and that said Letters Patent is hereby corrected as shown below:

On the title page: Item [73]

Assignee: Mazda Motor Corporation
            Hiroshima, Japan
                 and
           Jinen & Co., Ltd
           Tokyo, Japan - - - - -

Signed and Sealed this

Seventh Day of November, 2000

Attest:

Q. TODD DICKINSON

Attesting Officer            Director of Patents and Trademarks